United States Patent [19]

Tarjan

[11] Patent Number: 4,537,791

[45] Date of Patent: Aug. 27, 1985

[54] CARBON COATING OF GRAFTS OR CATHETERS

[75] Inventor: Peter P. Tarjan, Miami, Fla.

[73] Assignee: Cordis Corporation, Miami, Fla.

[21] Appl. No.: 594,037

[22] Filed: Mar. 27, 1984

[51] Int. Cl.$^3$ ............................ A01N 1/02; B05D 3/06
[52] U.S. Cl. ........................................ 427/2; 427/53.1;
427/249; 604/266; 604/280
[58] Field of Search ............... 604/265, 266, 280, 264;
427/2, 53.1, 249

[56] References Cited

U.S. PATENT DOCUMENTS

| | | | |
|---|---|---|---|
| 3,472,751 | 10/1969 | King | 204/192 |
| 3,526,906 | 9/1970 | De Laszlo | 128/334 X |
| 3,634,220 | 11/1972 | Goan | 204/164 |
| 3,677,795 | 7/1972 | Bokros et al. | 117/46 CG |
| 3,795,783 | 3/1974 | Plumat et al. | 219/121 EB |
| 3,877,080 | 4/1975 | Olcott | 264/42 X |
| 4,219,520 | 8/1980 | Kline | 264/129 |
| 4,254,180 | 3/1981 | Kline | 428/323 |
| 4,254,508 | 3/1981 | Bokros | 3/1.5 |
| 4,276,658 | 7/1981 | Hanson et al. | 3/1.5 |

OTHER PUBLICATIONS

Leyendecker, G. et al., *Laser Induced Chemical Vapor Deposition of Carbon*, Appl. Phys. Lett., 39(11), Dec. 1, 1981.

*Primary Examiner*—Michael R. Lusignan
*Attorney, Agent, or Firm*—George H. Gerstman

[57] ABSTRACT

An internally carbon coated graft or catheter and method of coating said grafts and catheters through the use of a carbon rod or a metal rod having a carbon pellet at its end coaxially positioned within the substrate's lumen. The graft may be concentrically supported by a metal tube. The rod and metal tube are placed into a vacuum chamber and the rod is subjected to a laser beam to cause the carbon end portion of the rod to transform into gaseous carbon and be deposited on the lumen of the substrate. The process is continued by moving the rod axially along the catheter or graft while being subjected to the effects of the laser beam.

15 Claims, 2 Drawing Figures

CARBON COATING OF GRAFTS OR CATHETERS

BACKGROUND OF THE INVENTION

This invention relates to the formation of a deposit of carbon within the lumen of a substrate and improved catheters, grafts, and the like, employing such internally coated carbon.

More specifically, but without restriction to the particular use which is shown and described, this invention relates to a device and method for coating the lumen of a substrate, such as used in grafts, catheters, and the like, used in living bodies.

It has been established that carbon coated surfaces used in vascular grafts or catheters, or other substrates for other uses are rendered less thrombogenic and more biocompatible by being coated with pure carbon. In the past, the outer surfaces of catheters and grafts could be more readily coated by RF sputtering techniques. The processes by which substrates are coated with carbon externally are not satisfactory to deposit carbon in the lumen of the device. In certain applications of catheters or grafts, it is much more critical that the lumen be rendered non-thrombogenic than is the exterior surface. In fact, if the substrate is a vascular graft, it is apparent that there is little reason to coat the exterior with carbon, but is highly advantageous that the lumen surface be so coated to prevent clogging by clotted blood.

In the employment of vessels leading to and from the heart, mechanical means to prevent or correct clogging have been, in many instances, ineffective. Often cracks or other discontinuites may occur through such techniques resulting in subsequent clogging. By carbon coating the lumen of a graft or similar vessel, the necessity of mechanically operating on implanted grafts, catheters, and the like to prevent such problems would be largely alleviated.

The coating of the lumen with carbon has presented difficult problems in the past. The use of heat to deposit the carbon can adversely affect the material of the catheter, graft, and the like. In addition, no prior art technique has been able to attain a good bond between the carbon and the internal surface which is also capable of maintaining a carbon interface between the catheter and the substance in the lumen, such as blood, and the like. Finally, it is extremely difficult to provide a uniform thin coating of the carbon within the lumen.

SUMMARY OF THE INVENTION

It is therefore an object of this invention to provide a substrate having a carbon coated lumen.

Another object of this invention is to provide an improved method of coating a substrate, such as a catheter, graft, and the like with carbon.

A further object of this invention is to improve the technique by which the lumen of a substrate is coated with carbon.

A further object of the invention is to internally coat the surface of a catheter, graft, and the like without adversely effecting the material of the vessel.

Still another object of this invention is to attain a superior bond of the layer of carbon deposited on the surface of a substrate.

A still further object of this invention is to provide a uniform thin coating of carbon on the surface of a substrate.

These and other objects are accomplished in accordance with the invention, wherein there is provided an improved catheter, graft, or similar vessel having a carbon coated lumen for less thrombogenicity and better biocompatibility. The substrate of the invention is produced by applying heat to a carbon material within the lumen in the presence of a heat sink. The heat sink serves to prevent damage of the lumen being coated by reducing the temperature of the process and/or further controlling the relative position of the carbon to the lumen. The heat is applied through the use of a laser beam to cause a carbon rod, pellet, and the like to vaporize into a gaseous carbon and be deposited on the internal surface. To attain a uniform coating, the carbon material is moved through the lumen during the application of heat.

BRIEF DESCRIPTION OF THE DRAWINGS

Further objects of the invention, together with additional features contributing thereto and advantages accruing therefrom, will be apparent from the following description of preferred embodiments of the invention, which are shown in the accompanying figures, wherein.

DESCRIPTION OF THE PREFERRED EMBODIMENTS

Figure 1:
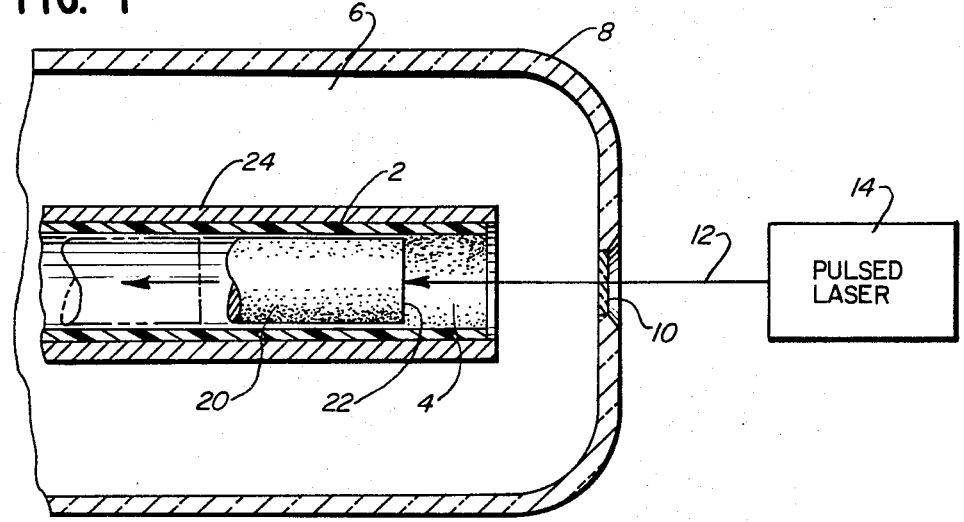
FIG. 1 is a schematic view of a first embodiment of the invention for coating the lumen of a substrate with carbon.

Referring now to FIG. 1 of the drawing, there is illustrated a schematic view of a catheter, graft, or other similar vessel 2 undergoing the method of the invention of applying a coating of carbon in the lumen 4 in accordance with the first embodiment of the invention. As shown in FIG. 1, the catheter 2 is positioned within a vacuum chamber 6 created by a suitable housing 8. The housing 8 may be provided with a window 10 to allow the light beam 12 of a laser 14 to be directed axially of the catheter 2. Although the laser 14 is shown in FIG. 1 as being a pulsed laser, it is within the scope of the invention to employ a steady light beam from a laser source. A carbon rod 20 having an end 22 is coaxially disposed in the lumen 4. Since the catheter 2 or other similar substrate is often flexible, a heat sink 24 of any suitable material, such as a metal, concentrically surrounds the exterior surface of the catheter 2. Heat sink 24 acts as a mechanical support of the catheter to alleviate the problems of damaging contact between the rod and the catheter wall by maintaining the vessel in a straight configuration.

The tube 24 also serves as a heat sink to protect the catheter 2 during the application of heat to the carbon rod 20 through means of a pulsed laser 14. Since the catheter or other body 2 may comprise a polyurethane, silicone rubber, polyethylene, Teflon and the like, the heat sink 2 alleviates the problem of damage by the high intensity beam. The beam of the laser 12 is directed against the end 22 in a manner that a localized portion of the end 22 is converted into a gaseous phase and these atoms then impact on the wall of the lumen 4 which typically may be within 0.5–3 mm from the center of the rod. Since carbon sublimates around 3,500° C., the end of the beam may be preferably a highly focused pulsed laser 14, but other laser systems capable of elevating the temperature to the necessary level may be used as previously stated. The placement of the catheter within the vacuum chamber insures a free path for the gaseous carbon atoms and allows them to deposit on the wall of the catheter. It is a function of the heat sink 24 to maintain the catheter or graft 2 at or below the temperature at which its material is damaged. The temperature of catheter 2 can also be protected by selecting appropriate intervals between the pulses of laser 14 that inhibit damaging heat levels to be generated. Further temperature control can be provided by an appropriate temperature sensor (not shown), such as an infrared temperature sensor capable of monitoring the magnitude of the temperature of the catheter.

To attain a uniform layer of carbon particles in the lumen, the rod 20 is axially moved at a predetermined rate through the concentric catheter 2 as shown, while the laser beam 12 is directed against the end of the carbon rod. Obviously, the extent of movement of the rod is governed by the length of the lumen to be coated with carbon, generally the entire length. Any suitable means may be employed to cause axial movement of the rod during the process. It is possible that the rod further could be rotated, if desired, to insure a uniform coating under certain situations.

In the previous description, it was described that the pulsed laser is directed through a window 10 in the housing 8, but it is possible to transmit the laser beam against the end 22 by means of fiber optics and the like. It is also possible that the beam applied to deposit carbon on the lumen may be provided by beams other than those produced by a laser where appropriate.

In order to obtain superior bonding of the carbon to the substrate, the coated lumen 4 may be irradiated with gamma rays to excite free radicals at the surface. Alternatively, the coated lumen 4 may be irradiated with non-coherent ultraviolet or visible light transmitted by a fiber optic. The non-coherency is required to disperse the beam on the lumen wall. The fiber optic and the substrate 2 should be moved relative to each other, axially and rotationally, during the irradiating process. However, while the coating generally requires pauses between pulses, the bonding process irradiation may be continuous.

Figure 2:
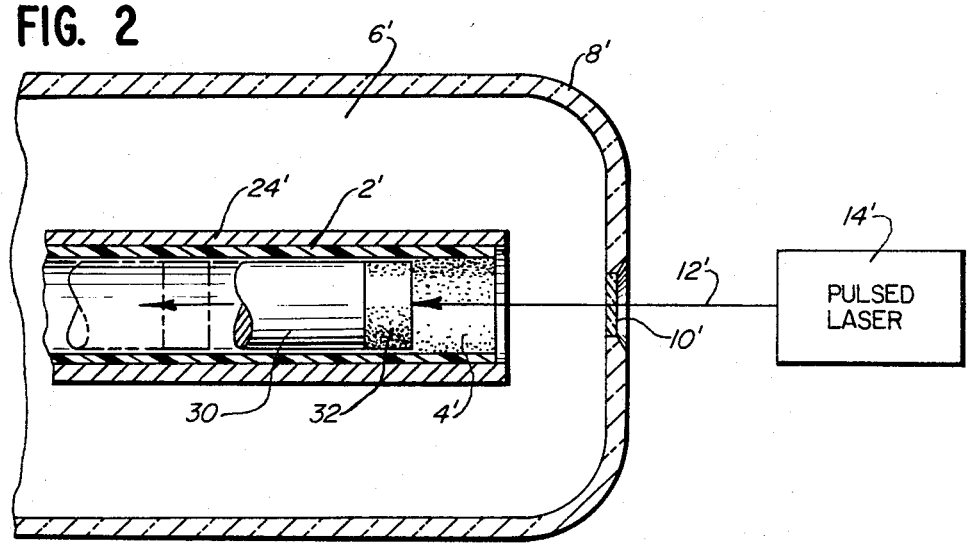
FIG. 2 is a schematic view of a second embodiment of the invention for coating the lumen of a substrate with carbon.

Referring now to FIG. 2, there is illustrated a second embodiment of the invention for applying carbon to the lumen of a substrate. For convenience of illustration, some of the elements which are shown in FIG. 2 and are similar in means and material to the elements of FIG. 1, are designated by the same reference numeral with a "prime" indication. In FIG. 2, the catheter 2' is positioned within a vacuum chamber 6' created by a suitable housing 8'. The housing 8' may be provided with a window 10' to allow the light beam 12' of a laser 14', such as a pulsed type, to be directed axially of the catheter 2'. A heat sink 24' of any suitable material, such as a metal, concentrically surrounds the exterior surface of the catheter 2'. Heat sink 24' acts as a mechanical support of the catheter to alleviate the problems of damaging contact between the heated carbon and the catheter wall by maintaining the vessel in a straight configuration.

The tube 24' also serves as a heat sink to protect the catheter 2' during the application of heat to the carbon rod 20' through means of a pulsed laser 14'. In the embodiment of FIG. 2, a carbon rod is replaced by an aluminum or other metal rod 30 having a pellet 32 of carbon affixed to its end. The aluminum rod serves as an enhanced heat conductor. As a result, heat is conducted efficiently away from the heated carbon during application of beam 12' against pellet 32 for cooling the carbon and increasing the duty cycle possible.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of coating an internal surface of a tube having a lumen comprising the steps of
    positioning a carbon body within the lumen of the tube to be coated;
    applying a beam of energy to said carbon body and causing the creation of gaseous carbon atoms to be deposited on the internal surface forming said lumen; and
    causing relative movement between the internal surface and the carbon body during application of said beam.

2. The method according to claim 1 wherein said beam is produced by a laser device.

3. The method according to claim 1 wherein said beam is applied to said carbon body in a vacuum.

4. The method according to claim 1 further comprising the step of irradiating the coated surface with selected rays to excite free radicals at said surface and to obtain superior bonding.

5. The method according to claim 1 further comprising the step of positioning a heat sink adjacent said tube during application of said beam.

6. The method according to claim 5 comprising the step of positioning said heat sink concentrically around said tube.

7. The method according to claim 5 further comprising the step of positioning said heat sink within said lumen adjacent said carbon body.

8. The method according to claim 4 in which the selected rays are one of gamma rays, non-coherent ultraviolet rays and visible light.

9. A method of coating the lumen of a tubular substrate comprising the steps of
    surrounding the substrate with a tubular heat sink;
    inserting a rod having at least a portion formed from carbon in the lumen of the substrate;
    placing the substrate, heat sink and rod into a chamber;
    applying a laser beam to said at least a portion of the rod for vaporizing the carbon and depositing the vaporized carbon in the lumen; and
    causing relative movement between the lumen surface and the rod during application of the laser beam.

10. The method according to claim 9 further including the step of moving the rod axially of said lumen.

11. The method according to claim 9 further comprising the step of creating a vacuum in said chamber.

12. The method according to claim 9 comprising the step of inserting a carbon rod into said lumen.

13. The method according to claim 9 comprising the step of inserting a metal rod into said lumen having carbon affixed to an end of the rod.

14. The method according to claim 9 further comprising the step of irradiating the coated surface with selected rays to excite free radicals at said surface and to obtain superior bonding.

15. The method according to claim 14 in which the selected rays are one of gamma rays, non-coherent ultraviolet rays and visible light.

* * * * *